(12) United States Patent
Codella et al.

(10) Patent No.: US 10,255,674 B2
(45) Date of Patent: Apr. 9, 2019

(54) SURFACE REFLECTANCE REDUCTION IN IMAGES USING NON-SPECULAR PORTION REPLACEMENT

(71) Applicant: INTERNATIONAL BUSINESS MACHINES CORPORATION, Armonk, NY (US)

(72) Inventors: Noel C. Codella, White Plains, NY (US); Chung-Ching Lin, White Plains, NY (US); Sharathchandra U. Pankanti, Darien, CT (US); Nalini K. Ratha, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/164,282

(22) Filed: May 25, 2016

(65) Prior Publication Data
US 2017/0345143 A1 Nov. 30, 2017

(51) Int. Cl.
G06K 9/00 (2006.01)
G06T 7/00 (2017.01)
G06T 3/40 (2006.01)
A61B 5/00 (2006.01)

(52) U.S. Cl.
CPC .......... *G06T 7/0012* (2013.01); *A61B 5/0013* (2013.01); *A61B 5/0077* (2013.01); *A61B 5/444* (2013.01); *A61B 5/6898* (2013.01); *G06T 3/4038* (2013.01); *G06T 2207/10016* (2013.01); *G06T 2207/30088* (2013.01); *G06T 2207/30096* (2013.01)

(58) Field of Classification Search
None
See application file for complete search history.

(56) References Cited

U.S. PATENT DOCUMENTS 6,208,749 B1 * 3/2001 Gutkowicz-Krusin ...... A61B 5/442
356/303
8,498,460 B2 * 7/2013 Patwardhan ......... A61B 5/0077
382/128

(Continued)

FOREIGN PATENT DOCUMENTS

EP 2223650 A1 9/2010

OTHER PUBLICATIONS

Brown, et al. "Recognising Panoramas," Department of Computer Science, University of British Columbia, Vancouver, Canada, pp. 1-8.

(Continued)

*Primary Examiner* — Tahmina N Ansari
(74) *Attorney, Agent, or Firm* — Cantor Colburn LLP; Rahan Uddin

(57) ABSTRACT

Embodiments include method, systems and computer program products for reducing surface reflectance, for example in a photograph. Aspects include receiving an image set containing a plurality of images of an object. Aspects also include determining geometric transformations for the images and constructing a panorama of the object from the images using the geometric transformations. Aspects also include replacing a portion in the panorama with a corresponding replacement portion from the image set.

17 Claims, 12 Drawing Sheets

(56) References Cited

U.S. PATENT DOCUMENTS

| | | |
|---|---|---|
| 2002/0173780 A1* | 11/2002 | Altshuler ............. A61B 18/203 |
| | | 606/9 |
| 2003/0091226 A1* | 5/2003 | Cahill ................ G06K 9/00201 |
| | | 382/154 |
| 2007/0003164 A1* | 1/2007 | Takata .................... G06T 7/254 |
| | | 382/284 |
| 2007/0211343 A1 | 9/2007 | Clark et al. |
| 2008/0165266 A1 | 7/2008 | Jenkins |
| 2008/0194928 A1 | 8/2008 | Bandic et al. |
| 2010/0033501 A1 | 2/2010 | Whitesell et al. |
| 2011/0206254 A1* | 8/2011 | Patwardhan ......... A61B 5/0077 |
| | | 382/128 |
| 2012/0157800 A1 | 6/2012 | Tschen |
| 2014/0104577 A1 | 4/2014 | Kaneda |
| 2014/0316235 A1 | 10/2014 | Davis et al. |

OTHER PUBLICATIONS

Lowe, David G. "Distinctive Image Features from Scale-Invariant Keypoints," Computer Science Department University of British Columbia Vancouver, B.C., Canada, Jan. 5, 2004, pp. 1-28.

Vasconcelos, et al. "Automatic Reflection Detection on Dermatological Images Acquired via Mobile Devices," http://www.city.ac.uk/, 2014, pp. 1-6.

* cited by examiner

SURFACE REFLECTANCE REDUCTION IN IMAGES USING NON-SPECULAR PORTION REPLACEMENT

BACKGROUND

The present disclosure relates generally to reduction of surface reflectance in photographic and other images, and more specifically to methods, systems and computer program products for reducing surface reflectance in images using standard camera equipment.

Photography using standard camera equipment can result in undesirable surface reflections (also referred to as surface reflectance) in captured images caused by lighting of the camera or other sources. Such reflections can obscure distinct areas from the image and can interfere with downstream applications.

For example, one application sensitive to such surface reflectance is the screening of skin for skin cancer. Unaided visual inspection of skin features by dermatologists for the detection of skin cancers can have a diagnostic accuracy of around 60%. To improve diagnostic accuracy, dermoscopic imaging was introduced. Dermoscopic imaging, or dermoscopy, is a technique that involves placing a high-resolution magnifying imaging device in contact with the skin. Dermoscopic imaging has been shown to improve recognition performance over unaided visual inspection by up to 50%, resulting in diagnostic accuracies of between 75%-84%.

The generation of suitable photographic images of skin for use in diagnostic dermatological screening applications involves special challenges due to the sometimes very high reflectance of the skin, which can distort the captured image and interfere with diagnostics. Even where lighting is controlled, special procedures and tools are required to remove surface skin reflectance from the captured image in conventional methods. Conventional procedures to remove areas of surface skin reflectance, also referred to as specular reflections, can be burdensome and can require costly equipment. For example, polarization techniques to remove reflectance require use of special filters and, moreover, require controlled lighting conditions that involve a light source of fixed and known direction. Such techniques, for example, cannot be used outdoors where multiple light sources from varying locations exist. In some cases, for example, costly dermascopes can be used. In other conventional methods, where special filters and/or dermascopes are not available, specular reflections can be reduced or eliminated by applying a layer of oil to the skin to act as a medium between a camera lens and the skin, which can be undesirable to a patient.

SUMMARY

In accordance with an embodiment, a computer-implemented method for reducing surface reflectance is provided. The method includes receiving, by a processor, an image set comprising a plurality of images of an object. The method also includes determining a plurality of geometric transformations for the plurality of images of the object. The method also includes constructing a panorama of the object from the plurality of images using the geometric transformations. The method also includes replacing one or more portions in the panorama with a corresponding replacement portion from the image set.

In accordance with another embodiment, a computer program product for reducing surface reflectance is provided. The computer program product includes a computer readable storage medium having program instructions embodied therewith, the program instructions executable by a processor to cause the processor to receive, by the processor, an image set comprising a plurality of images of an object. The processor is also configured to determine a plurality of geometric transformations for the plurality of images of the object. The processor is also configured to construct a panorama of the object from the plurality of images using the geometric transformations. The processor is also configured to replace one or more portions in the panorama with a corresponding replacement portion from the image set.

In accordance with a further embodiment, a processing system for reducing surface reflectance includes a processor in communication with one or more types of memory. The processor is configured to receive an image set comprising a plurality of images of an object. The processor is also configured to determine a plurality of geometric transformations for the plurality of images of the object. The processor is also configured to construct a panorama of the object from the plurality of images using the geometric transformations. The processor is also configured to replace one or more portions in the panorama with a corresponding replacement portion from the image set.

BRIEF DESCRIPTION OF THE DRAWINGS

The subject matter of the present disclosure is particularly pointed out and distinctly claimed in the claims at the conclusion of the specification. The foregoing and other features and advantages of the one or more embodiments disclosed herein are apparent from the following detailed description taken in conjunction with the accompanying drawings in which:

DETAILED DESCRIPTION

Figure 1:
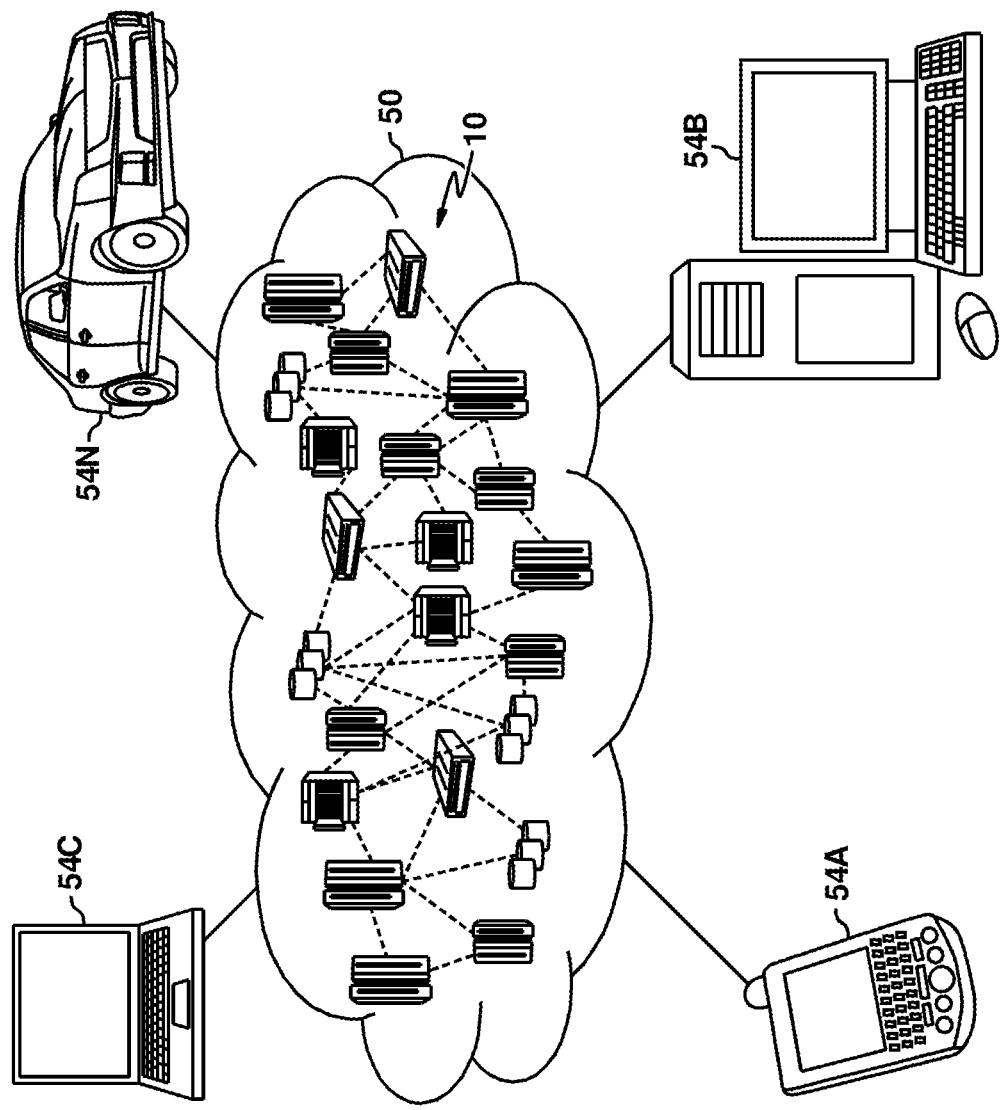
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
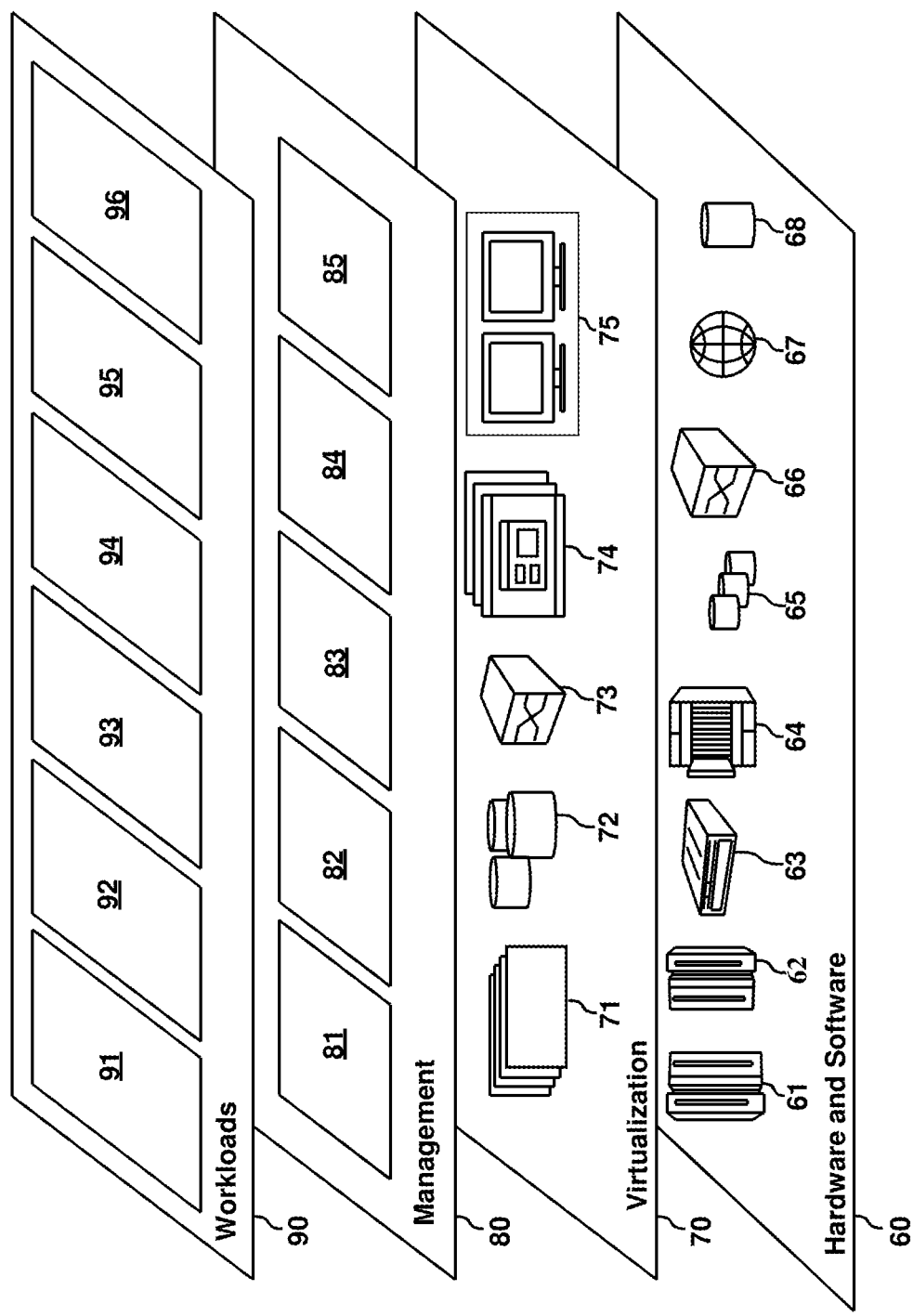
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and image processing 96.

In accordance with one or more embodiments of the disclosure, methods, systems and computer program products for reducing surface reflectance in photographs are provided.

Figure 3:
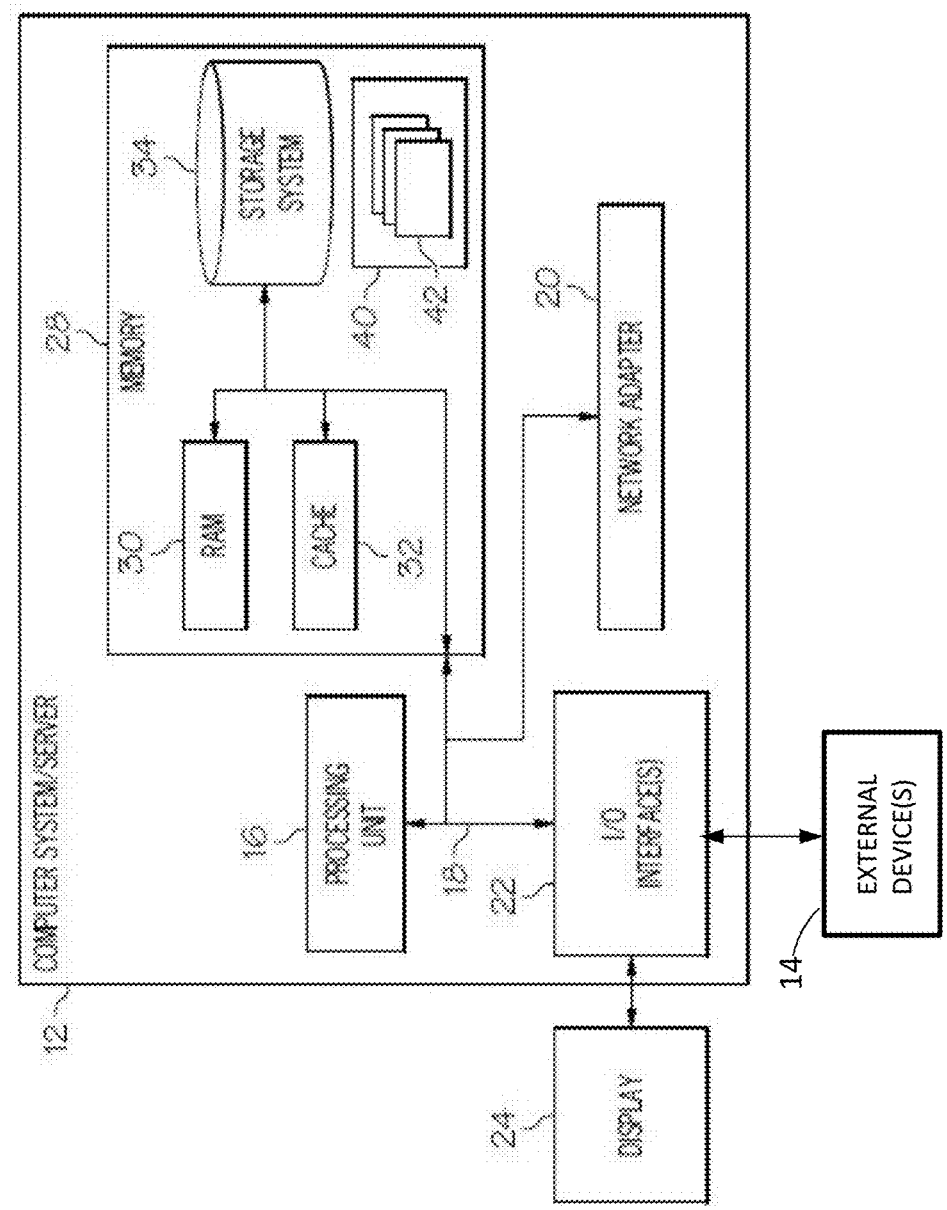
FIG. 3 is a computer system according to one or more embodiments.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in cloud computing node 100 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of the present disclosure, one or more embodiments provide systems and methodologies for reducing surface reflectance using a conventional camera. More specifically, the present disclosure provides reduced surface reflectance in images, by constructing a panorama image from an image set, wherein the image set contains multiple images and/or perspectives of an object, and then replacing specular portions of the panorama with corresponding nonspecular portions from the image set. More specifically, the systems and methodologies for reducing surface reflectance can identify specular regions, or regions with high surface reflectance and corresponding nonspecular regions from an image set and substitute the nonspecular regions for the specular regions. In one or more embodiments, specular regions having a brightness of greater than a given threshold, such as a threshold of 200 on each channel on the RGB scale, can be replaced with corresponding regions, for instance on a pixel by pixel basis, with corresponding regions from the image set with a brightness below the threshold.

Figure 4:
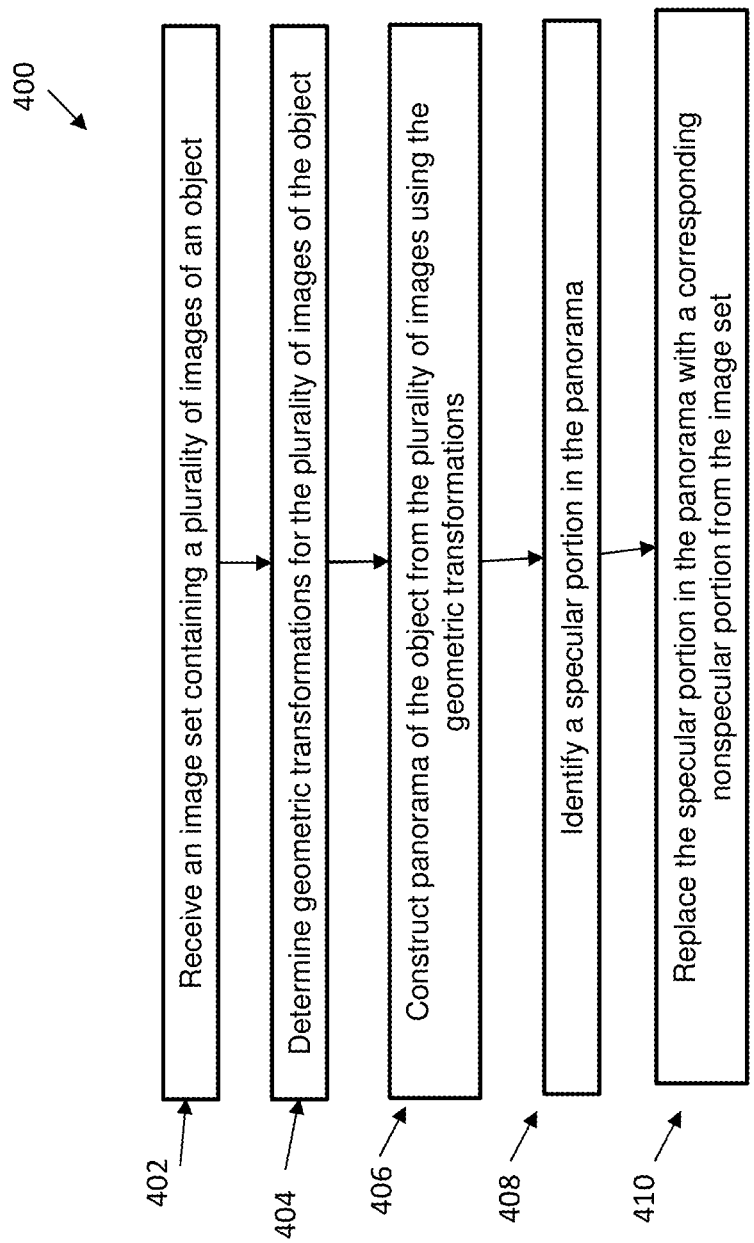
FIG. 4 is a flow diagram illustrating a method for reducing surface reflectance in images according to one or more embodiments.

Referring now to FIG. 4, a flow chart illustrating a method 400 for reducing surface reflectance in accordance with one or more embodiments is shown. As used in the present disclosure, the term image refers to a representation of an object in a chosen format, wherein the chosen format includes but is not limited to electronic data. The chosen format may be stored in an electronic storage medium and is capable of being manipulated by a processing device (e.g., a computer processor) and/or displayed through a visible medium (e.g., a display, photographic paper, etc.). As shown at block 402, the method 400 includes receiving an image set containing a plurality of images of an object. Next, as shown at block 404, the method 400 includes determining geometric transformations for the plurality of images of the object. As shown at block 406, the method 400 also includes constructing a panorama of the object from the plurality of images using the geometric transformations. In some embodiments, as shown at block 408, the method 400 optionally includes identifying a specular pixel in the panorama. Then, as shown at block 410, the method 400 includes replacing a specular portion in the panorama with a corresponding nonspecular portion from the image set.

As used herein, a panorama includes any wide-angle view or representation of an object up to and including a 360° degree viewing angle. In preferred embodiments, a panorama includes an angle up to and including a 180° degree viewing angle of an object, or a 90° degree viewing angle of an object, or a 60° degree viewing angle of an object.

In some embodiments, the image set containing a plurality of images of an object is an image set derived from a video of an object. For example, a video recording of an object can be taken, where the video captures the object from a plurality of angles or locations on the horizontal and/or vertical planes. The video recording can be subsequently split into an image set according to known methods. The video recording, for example, can include a zoom of the object, a pan of the object, and/or a tilting of a camera during recording.

In some embodiments, receiving a plurality of images of an object includes receiving a video recording of the object. In some embodiments, receiving a plurality of images of an object includes receiving a plurality of images that are derived from a video recording of an object.

Methods for determining geometric transformations are known to those of ordinary skill in the art. In accordance with the disclosure, any method for determining geometric transformations between image pairs can be used. Geometric transformations can be stored, for instance, as a 3×3 matrix or vector including scale, angle, and translation information. For example, a transform T can be stored as $T=T+(i, j, t_{ij})$ wherein i represents a first image of the image set, j represents a second image of the image set and $t_{ij}$ represents the estimated or actual geometric transform of images i and j.

As used herein, specular portion is understood to mean a portion of an image that contains a mirror-like reflection of light from a surface of the object that is the subject of the photograph. A nonspecular portion is understood to mean a portion of an image that does not contain a mirror-like reflection of light from a surface of the object that is the subject of the photograph.

Figure 5:
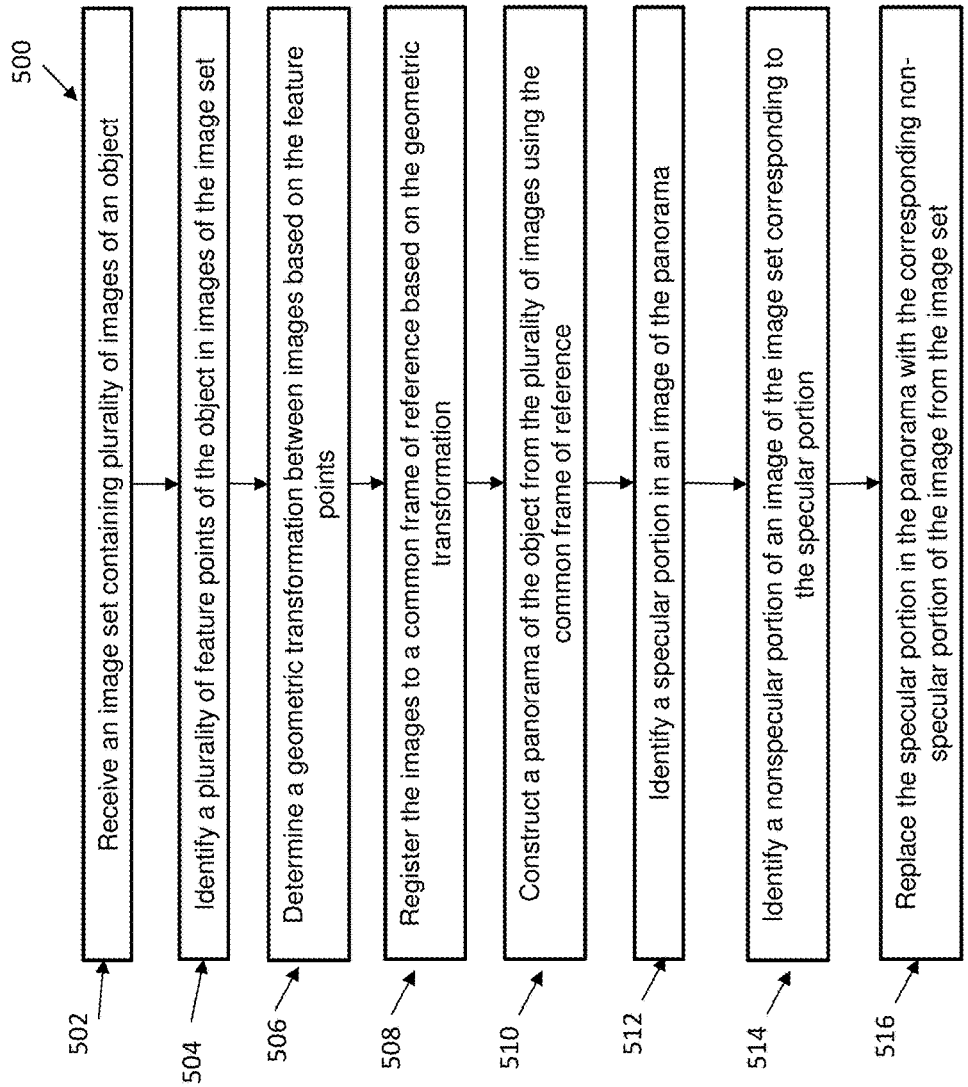
FIG. 5 is a flow diagram illustrating a method for reducing surface reflectance in images according to one or more embodiments.

FIG. 5 shows a method 500 for reducing surface reflectance in images according to another exemplary embodiment. In comparison, the method 500 shown in FIG. 5 is a more detailed implementation of the method 400 shown in FIG. 4. The method 500 includes, as shown at block 502, receiving an image set containing a plurality of images of an object. Next, as shown at block 504, the method 500 includes identifying a plurality of feature points of the object in images of the image set. The method 500 also includes, as shown at block 506, determining a geometric transformation between images of the image set. As shown at block 506, the geometric transformation can, in some embodiments, be based upon the feature points. As shown at block 508, the method 500 includes registering the images to a common frame of reference based upon the geometric transformation. Next, as shown at block 510, the method 500 includes constructing a panorama of the object from the plurality of images using the common frame of reference. The method 500 also includes, as shown at block 512, identifying a specular portion in an image of the panorama. As shown at block 514, the method 500 also includes identifying a nonspecular portion of an image in the image set corresponding to the specular portion. Then, as shown at block 516, the specular portion in the panorama is replaced with the corresponding nonspecular portion of the image from the image set.

In some embodiments, feature points include points that correspond to a unique feature or spatial location of the object, such as a corner of an object. Methods for determining feature points are known in the art. For example, feature points can include salient points or Scale Invariant Feature Transform (SIFT) points.

Figure 6:
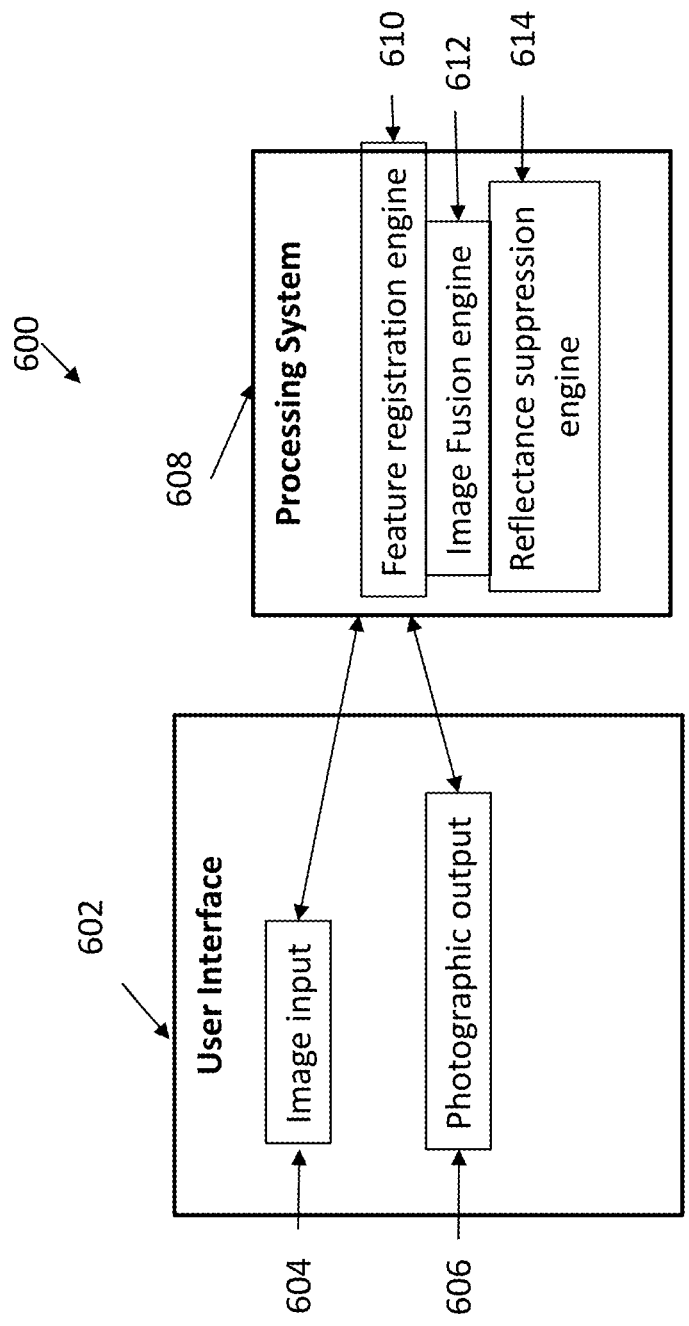
FIG. 6 is block diagram illustrating system for reducing surface reflectance in images according to one or more embodiments.

Referring now to FIG. 6, a block diagram of a system 600 for reducing surface reflectance in images according to one or more embodiments is illustrated. As illustrated, a user interface 602 includes an image input 604 and a photographic output 606. In one or more embodiments, the user interface can be a display on a phone, digital camera, smartphone, smartwatch, computer, tablet, or the like. The image input 604 can include any input system that can receive or collect a plurality of images of an object, such as a camera, or video camera. In a preferred embodiment, the image input 604 includes standard photographic equipment. In some embodiments, the image input does not include any photographic filters. In one or more embodiments, the system 600 includes a processing system 608. In some embodiments, the processing system 608 receives the image input from the user interface. In other embodiments, the processing system 608 receives the image input from another source.

In one or more embodiments, the processing system 608 contains a feature registration engine 610. The feature registration engine 610 can estimate or determine geometric transformations for image pairs received from the image input 604. In one or more embodiments, the processing system 608 contains an image fusion engine 612. The image fusion engine 612 can render images from the image input 604 into a panorama. In one or more embodiments, the processing system 608 contains a reflectance suppression engine 614. The reflectance suppression engine 612 can replace specular portions of an image with corresponding nonspecular portions from the image input 604. Photographic output 606 includes an image of the object processed according to one or more embodiments, such as an image or photograph of the object with specular reflections removed or reduced.

Figure 7:
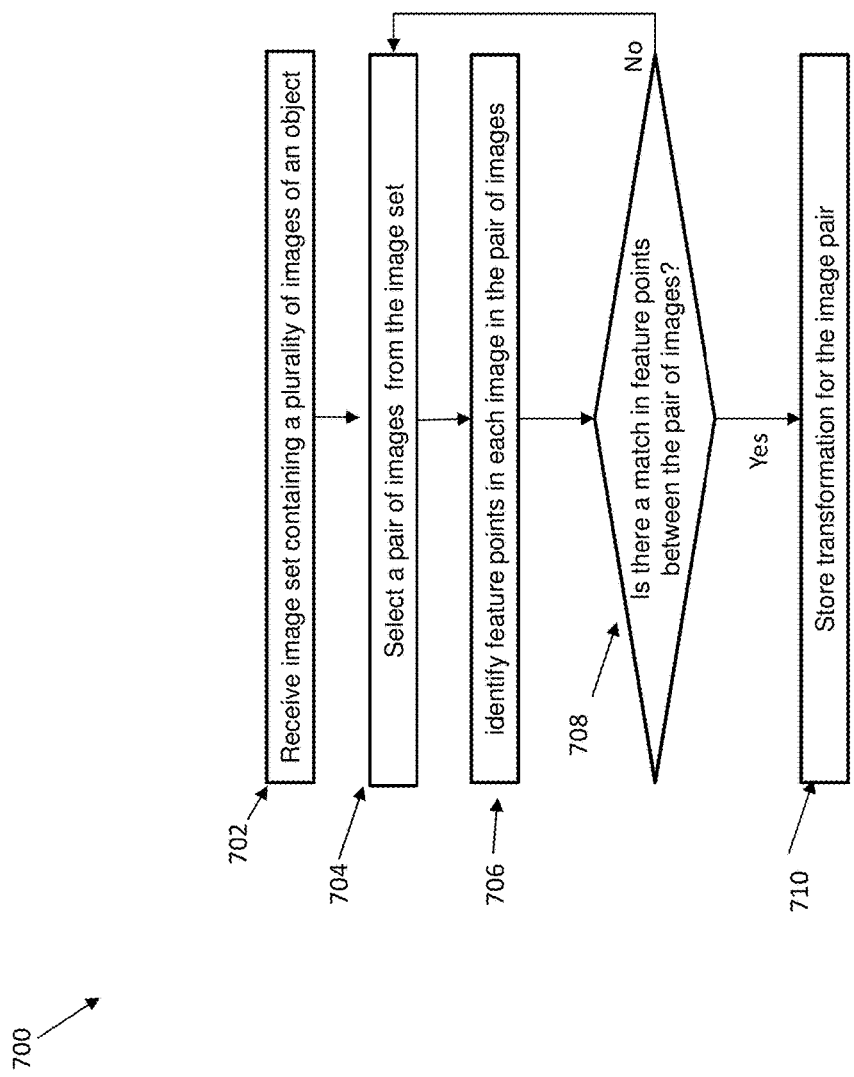
FIG. 7 is a flow diagram illustrating a method for estimating a geometric transformation among image pairs according to one or more embodiments.

Referring now to FIG. 7, a flow chart illustrating a method 700 for estimating a geometric transformation among image pairs according to one or more embodiments is shown. As shown at block 702, the method 700 includes receiving an image set containing a plurality of images of an object. Next, as shown at block 704, the method 700 includes selecting a pair of images from the image set. Then, as shown at block 706, the method 700 includes identifying feature points in each image in the pair of images. As shown at decision block 708, the method 700 includes determining whether there is a match in feature points between the pair of images. If there is a match in feature points between the pair of images, the method 700 proceeds to block 710 and stores a transformation for the image pair. If there is no match in feature points between the pair of images, the method 700 returns to block 704 and selects another pair of images from the image set. In some embodiments, after a transformation for the image pair is stored, the method can include selecting another pair of images from the image set, identifying feature points in each image of the pair of images, and determining whether there is a match in feature points between the pair of images.

Figure 8:
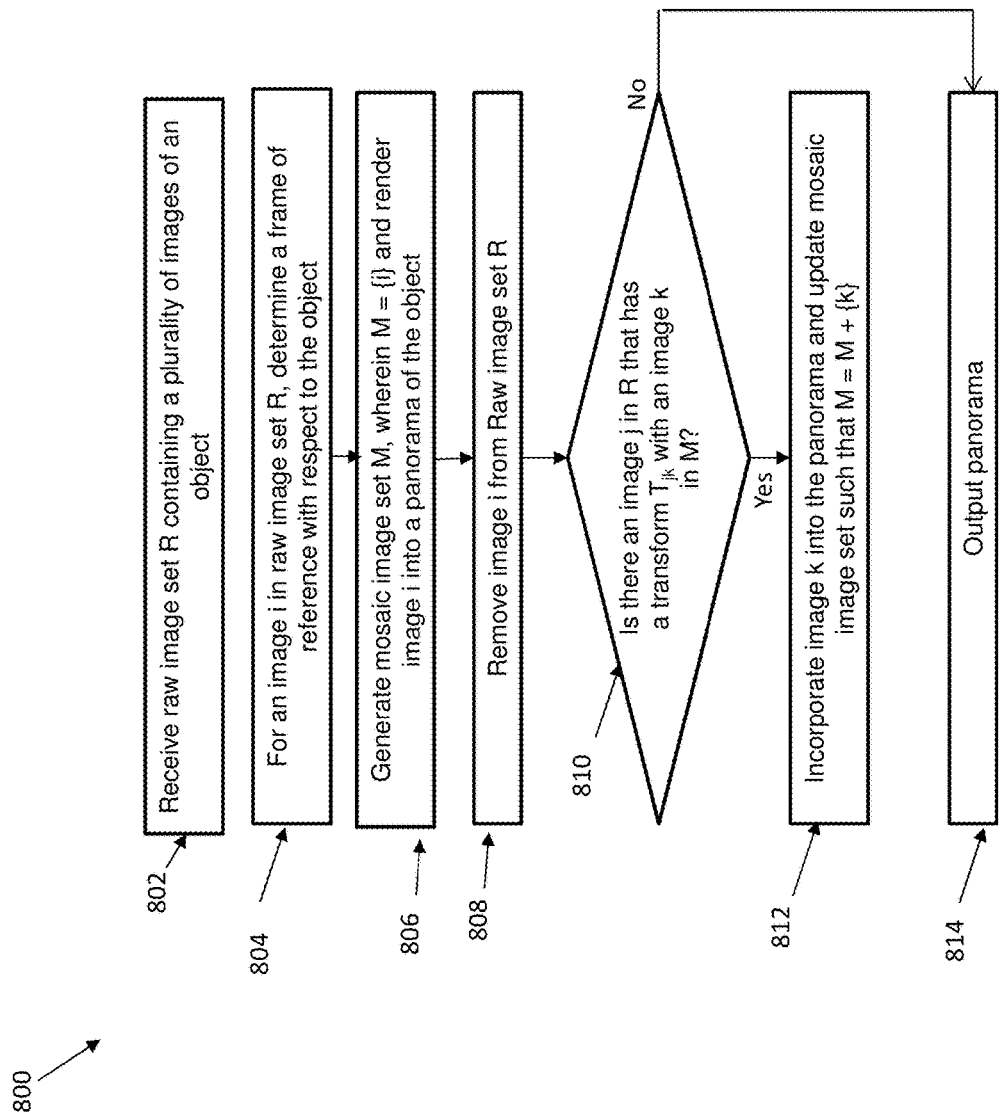
FIG. 8 is a flow diagram illustrating a method for constructing a panorama according to one or more embodiments.

With reference now to FIG. 8, a flow chart illustrating a method 800 for constructing a panorama according to one or more embodiments is shown. As shown at block 802, the method 800 includes receiving a raw image set R containing a plurality of images of an object. Next, as shown at block 804, the method 800 includes determining a frame of reference with respect to the object for an image i in the raw image set R. In some embodiments, a pixel by pixel analysis is conducted to identify all candidate pixels that can be used for a particular point in the resultant panorama. In some embodiments, for example, if a pixel in the panorama is determined to be brighter than other corresponding pixels from the raw image set R, the pixel can be replaced. In a preferred embodiment, image i is a single image. As shown at block 806, the method 800 includes generating a mosaic image set M, wherein M={i} and rendering image i into a panorama of the object. Then, as shown at block 808, the method 800 removes the image i from the raw image set R. Next, as shown at decision block 810, the method 800 includes determining whether there is an image j in R that has a transform $T_{jk}$ with an image k in M. If there is an image j in R that has a transform $T_{jk}$ with an image k in M, then the method 800 proceeds to block 812 and includes incorporating the image k into the panorama and updating the mosaic image set such that M=M+{k}. If there is not an image j in R that has a transform $T_{jk}$ with an image k in M, then the method 800 proceeds to block 814 and outputs the panorama.

In some embodiments, a specular portion of an image or panorama is identified. Identifying a specular portion can include finding all pixels in an image k with a brightness greater than t1, wherein t1 is a first brightness threshold. Next, in some embodiments, identifying a specular portion can include computing a binary mask of brighter than t1 pixels. Then, in accordance with some embodiments, identifying a specular portion can include running a connected components analysis. Then, in accordance with some embodiments, identifying a specular portion can include removing from the image connected components having a size smaller than s1, wherein s1 is a first size threshold. In some embodiments, a specular portion of pixels in an image k (sk) is the union of all pixels in the image that remain after connected components are removed.

In some embodiments, the method does not include identifying a specular portion. In such embodiments, for example, any extrinsic known methods can be employed to identify specular pixels. For example, in an embodiment where an extrinsic method is employed to identify specular pixels, all pixels can be designated candidate specular pixels. For example, a skin lesion can be detected and all pixels within the skin lesion can be designated candidate specular pixels.

In some embodiments, candidate specular pixels can be identified by automatically identifying specular pixels and/or manually identifying specular pixels. Candidate specular pixels can subsequently be used to identify specular portions as disclosed herein.

Figure 9:
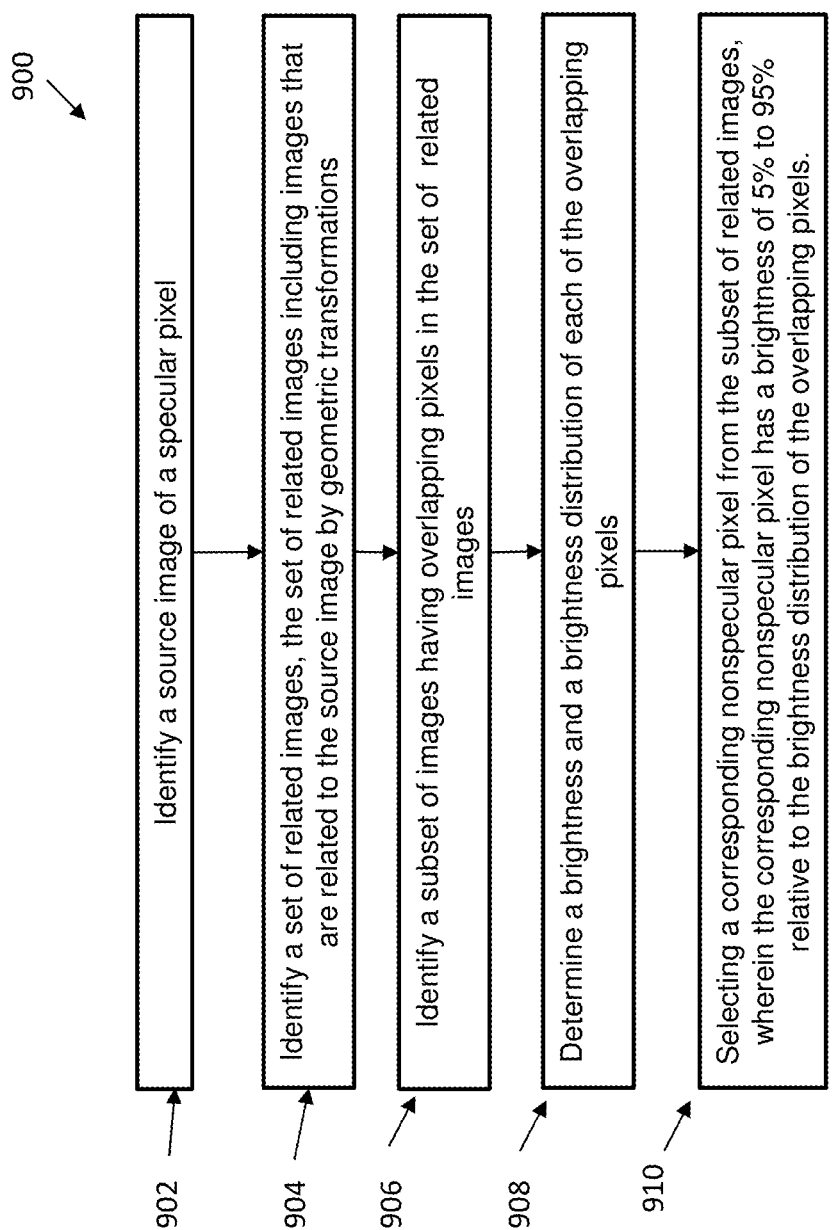
FIG. 9 is a flow diagram illustrating a method for replacing a specular pixel with a corresponding nonspecular pixel according to one or more embodiments.

FIG. 9 shows a method 900 for replacing a specular pixel with a corresponding nonspecular pixel according to one or more embodiments. As shown at block 902, the method 900 includes identifying a source image of a specular pixel. Next, the method 900 includes identifying a set of related images as shown in block 904, wherein the set of related images includes images that are related to the source image by geometric transformations. Then, as shown at block 906, the method 900 includes identifying a subset of images having overlapping pixels in the set of related images. In some embodiments, the method 900 also includes determining a brightness and a brightness distribution of each of the overlapping pixels, as shown at block 908. Then, as shown at 910, the method 900 can include selecting a corresponding nonspecular pixel from the subset of related images, wherein the corresponding nonspecular pixel has a brightness of 5% to 95% relative to the brightness distribution of the overlapping pixels.

For example, for each pixel $p_{uv}$ in specular s portion in image i, in some embodiments, replacing a specular portion includes finding all images {k} related to i by transform $t_{ik}$. Then, replacing a specular portion can include finding subset images {m} of {k} overlapping with $p_{uv}$ in s. A distribution can be determined of d={$_{n-=1, \ldots, |m|} p'_{uv}$} pixels corresponding to $p_{uv}$ from each of image kin {m}. Replacing a specular portion can also include assessing non-specular counterpart $p''_{uv}$ from d. In one embodiment, the top and bottom 2.5% of pixel intensities can then be removed from the distribution and/or the extreme (i.e., low and high) $2.5^{th}$ percentile of brightness of d can be removed. Then, replacing the specular portion can include replacing $p_{uv}$ with $p''_{uv}$. In one embodiment, the replacement uses average (arithmetic mean) brightness of ($p''_{uv}$).

In some embodiments, brightness is determined according to a RGB image channel scale, where each pixel can have a value of 0 to 255 on each of the red, green, and blue channels. In accordance with the RGB channel scale, for example, a value of greater than 200 in multiple channels, such as in all three channels, can be indicative of a specular reflection.

Figure 10B:
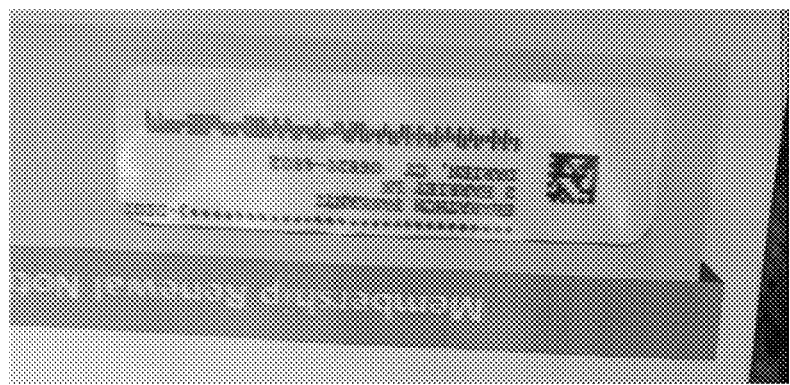
FIG. 10B is a photographic image of the object depicted in FIG. 10A, wherein the photographic image has undergone a method for reducing surface reflectance in accordance with one or more embodiments.
Figure 10A:
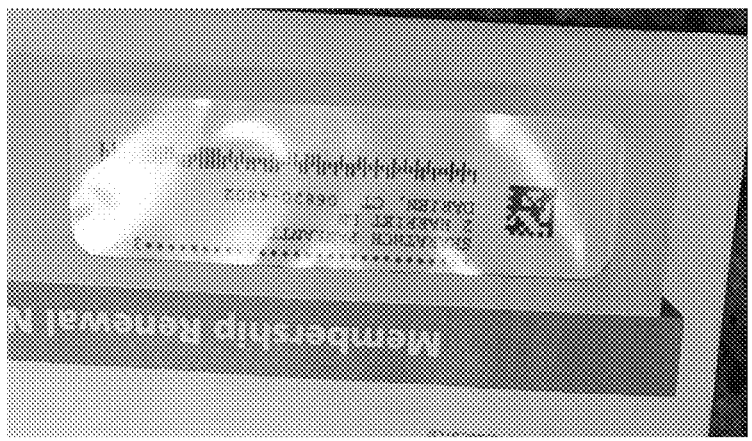
FIG. 10A is a photographic image of an object not subjected to any method for reducing specular reflections.

FIGS. 10A-10B depict photographs of an object, a portion of an envelope with a reflective window, generated according to various methods. FIG. 10A is a photograph of the object taken with ordinary camera equipment. FIG. 10B is a photograph of the same object shown in FIG. 10A, wherein the photograph was generated using a method according to one or more embodiments of the present disclosure. As is shown, the specular reflectance in the image shown in FIG. 10B is reduced in comparison with the image of the same object shown in FIG. 10A. As is illustrated, pixels having a brightness above a selected threshold can be replaced with pixels from an image set that have a brightness below the selected threshold according to one or more embodiments of the disclosure.

Figure 11:
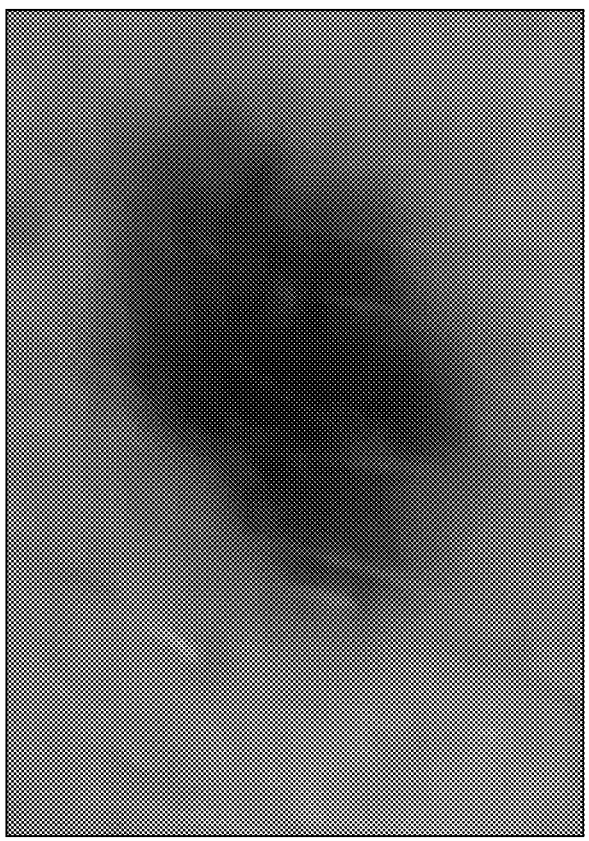
FIG. 11 is a 221 by 154 pixel photographic image of a skin lesion depicted, wherein the photographic image has undergone a method for reducing surface reflectance in accordance with one or more embodiments.

FIG. 11 depicts a 221×154 image of a skin lesion generated using a method according to one or more embodiments of the present disclosure. The image is a panorama constructed from an image set derived from a video, in which pixels having a brightness of greater than 200 on all of the three channels on the RGB channel scale have been replaced with corresponding pixels having a brightness below 200 on at least two channels of the RGB channel scale.

Figure 12:
FIG. 12 is a 171 by 149 pixel photograph of another skin lesion, wherein the photograph has undergone a method for reducing surface reflectance in accordance with one or more embodiments.

FIG. 12 depicts a 171×149 image of another skin lesion generated using a method according to one or more embodiments of the present disclosure. The image is a panorama constructed from an image set derived from a video, in which pixels having a brightness of greater than 200 on all of the three channels on the RGB channel scale have been replaced with corresponding pixels having a brightness below 200 on at least two channels of the RGB channel scale.

Thus, it can be seen from the forgoing detailed description that one or more embodiments of the present disclosure provide technical effects and benefits. The present disclosure provides reduced surface reflectance in images taken with ordinary camera and video equipment, reducing or eliminating the need for costly filters or camera equipment and/or cumbersome photographic techniques. For instance, in one or more embodiments, a dermatological patient can use a smartphone to generate an image of a skin lesion suitable for diagnostic purposes by a health care professional, potentially eliminating the need for an in-office visit.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for reducing surface reflectance, the method comprising:
   receiving, by a processor, an image set comprising a plurality of images of an object;
   determining a plurality of geometric transformations for the plurality of images of the object;
   constructing a panorama of the object from the plurality of images using the geometric transformations;
   replacing one or more specular portions in the panorama with a corresponding one or more replacement non-specular portions from the image set,
   wherein the replacing of the one or more specular portions in the panorama with the corresponding one or more replacement non-specular portions from the image set comprises:
   identifying, from source images respectively corresponding to the one or more specular portions, related images comprising one or more images related to the source images by the geometric transformations which have one or more overlapping portions that overlap with the one or more specular portions; and
   selecting the corresponding one or more replacement non-specular portions from the one or more overlapping portions of the related images that have lesser brightness than of each of the one or more specular portions.

2. The computer-implemented method of claim 1, wherein the plurality of images represent a skin surface.

3. The computer-implemented method of claim 1, wherein the object is a skin lesion.

4. The computer-implemented method of claim 1, wherein the image set is derived from a mobile device.

5. The computer-implemented method of claim 1, wherein the processor is located in a portable device.

6. The computer-implemented method of claim 4, wherein the portable device is a network connected device.

7. The computer-implemented method of claim 4, wherein the portable device is a network disconnected device.

8. The computer-implemented method of claim 1, wherein determining a geometric transformation between the polarity of images comprises:
   selecting a pair of images from the image set, the pair of images comprising a pair first image and a pair second image;
   identifying a plurality of feature points of the object in the pair first image;
   identifying a plurality of feature points of the object in the pair second image; and
   responsive to a determination that one of the feature points in the first pair image matches one of the feature points in the second pair image, storing a pair transform for the pair of images.

9. The computer-implemented method of claim 1, wherein constructing the panorama of the object comprises:
   selecting a first image from the image set;
   determining a frame of reference with respect to the first image;
   generating a mosaic image set comprising the first image;
   rendering the first image into the panorama;
   removing the first image from the image set;
   identifying a second image in the image set, the second image having a geometric transformation relative to the first image and the second image; and
   rendering the second image into the panorama using the geometric transformation relative to the first image and the second image.

10. The computer-implemented method of claim 1, wherein the corresponding non-specular portions have a brightness of 5% to 95% relative to a brightness distribution of the overlapping portions.

11. The computer-implemented method of claim 1, wherein the corresponding non-specular portions have a brightness within 25% of the median of a brightness distribution of the overlapping portions.

12. The computer-implemented method of claim 1, further comprising identifying a specular portion of the panorama.

13. The computer-implemented method of claim 12, wherein identifying a specular portion of the panorama comprises:

calculating a specular pixel set, the specular pixel set comprising all specular pixels in the panorama, the specular pixels having a red channel brightness greater than 200, a green channel brightness greater than 200, and a blue channel brightness greater than 200 on a brightness scale of 0 to 255;

determining a connectivity of the specular pixels; and removing from the specular pixel set all specular pixels having a connectivity below a size threshold;

wherein the specular portion of the panorama comprises a connected set of pixels from the specular pixel set.

14. A computer program product for reducing surface reflectance, the computer program product comprising a non-transitory computer readable storage medium having program instructions embodied therewith, the program instructions executable by a processor to cause the processor to:

receive, by the processor, an image set comprising a plurality of images of an object;

determine, by the processor, a plurality of geometric transformations for the plurality of images of the object;

construct, by the processor, a panorama of the object from the plurality of images using the geometric transformations;

replace, by the processor, one or more specular portions in the panorama with a corresponding one or more replacement non-specular portion from the image set, wherein a replacement of the one or more specular portions in the panorama with the corresponding one or more replacement non-specular portions from the image set comprises:

an identification, from source images respectively corresponding to the one or more specular portions, of related images comprising one or more images related to the source images by the geometric transformations which have one or more overlapping portions that overlap with the one or more specular portions; and a selection of the corresponding one or more replacement non-specular portions from the one or more overlapping portions of the related images that have lesser brightness than of each of the one or more specular portions.

15. The computer program product of claim 14, wherein a determination of a geometric transformation between the plurality of images comprises:

a selection of a pair of images from the image set, the pair of images comprising a pair first image and a pair second image;

an identification of a plurality of feature points of the object in the pair first image;

an identification of a plurality of feature points of the object in the pair second image; and responsive to a determination that one of the feature points in the first pair image matches one of the feature points in the second pair image, storage of a pair transform for the pair of images.

16. The computer program product of claim 14, wherein construction of the panorama of the object comprises:

a selection of a first image from the image set;

a determination of a frame of reference with respect to the first image;

a generation of a mosaic image set comprising the first image;

a rendering of the first image into the panorama;

removal the first image from the image set;

an identification of a second image in the image set, the second image having a geometric transformation relative to the first image and the second image; and a rendering of the second image into the panorama using the geometric transformation relative to the first image and the second image.

17. A processing system for reducing surface reflectance, comprising:

a processor in communication with one or more types of memory, the processor configured to:

receive an image set comprising a plurality of images of an object;

determine a plurality of geometric transformations for the plurality of images of the object;

construct a panorama of the object from the plurality of images using the geometric transformations;

replace one more specular portions in the panorama with corresponding one or more replacement non-specular portions from the image set, wherein a replacement of the one or more specular portions in the panorama with the corresponding one or more replacement non-specular portions from the image set comprises:

an identification, from source images respectively corresponding to the one or more specular portions, of related images comprising one or more images related to the source images by the geometric transformations which have one or more overlapping portions that overlap with the one or more specular portions; and a selection of the corresponding one or more replacement non-specular portions from the one or more overlapping portions of the related images that have lesser brightness than of each of the one or more specular portions.

* * * * *